(12) United States Patent
Okada (10) Patent No.: US 7,968,819 B2
(45) Date of Patent: Jun. 28, 2011

(54) MICRODISSECTION APPARATUS AND METHOD

(75) Inventor: Naobumi Okada, Asaka (JP)

(73) Assignee: Olympus Corporation, Tokyo (JP)

( * ) Notice: Subject to any disclaimer, the term of this patent is extended or adjusted under 35 U.S.C. 154(b) by 989 days.

(21) Appl. No.: 10/696,532

(22) Filed: Oct. 28, 2003

(65) Prior Publication Data

US 2004/0084426 A1  May 6, 2004

(30) Foreign Application Priority Data

Oct. 31, 2002 (JP) .................................. 2002-317997
Sep. 30, 2003 (JP) .................................. 2003-341157

(51) Int. Cl.
*B23K 26/14* (2006.01)
*B23K 26/16* (2006.01)

(52) U.S. Cl. .......... 219/121.67; 219/121.68; 219/121.69

(58) Field of Classification Search ............. 219/121.67, 219/121.68, 121.69, 121.73, 121.6
See application file for complete search history.

(56) References Cited

U.S. PATENT DOCUMENTS

| | | | |
|---|---|---|---|
| 4,842,782 A * | 6/1989 | Portney et al. | ................ 264/1.37 |
| 5,208,437 A | 5/1993 | Miyauchi et al. | |
| 5,859,699 A | 1/1999 | Baer et al. | |
| 5,998,129 A | 12/1999 | Schutze et al. | |
| 6,040,139 A | 3/2000 | Bova | |
| 6,100,051 A | 8/2000 | Goldstein et al. | |
| 6,215,550 B1 | 4/2001 | Baer et al. | |
| 6,251,516 B1 * | 6/2001 | Bonner et al. | ................ 428/346 |
| 6,316,234 B1 | 11/2001 | Bova | |
| 6,639,657 B2 * | 10/2003 | Baer et al. | ......................... 356/36 |
| 6,753,161 B2 * | 6/2004 | Koller et al. | ................. 435/40.5 |
| 6,756,586 B2 * | 6/2004 | Caprioli | ......................... 250/282 |
| 6,787,301 B2 | 9/2004 | Ganser et al. | |
| 6,870,625 B1 * | 3/2005 | Baer et al. | ..................... 356/417 |
| 2002/0048747 A1 | 4/2002 | Ganser | |
| 2002/0056345 A1 | 5/2002 | Ganser et al. | |

FOREIGN PATENT DOCUMENTS

| | | |
|---|---|---|
| JP | 4-23453 A | 1/1992 |
| JP | 8-174242 A | 7/1996 |
| JP | 9-90232 A | 4/1997 |
| JP | 9-206965 A | 8/1997 |
| JP | 2000-266649 A | 9/2000 |
| JP | 2002-174778 A | 6/2002 |

OTHER PUBLICATIONS

Japanese Office Action dated Sep. 8, 2009 (3 pages), and English translation thereof (4 pages), issued in counterpart Japanese Application Serial No. 2003-341157.

* cited by examiner

*Primary Examiner* — M. Alexandra Elve
(74) *Attorney, Agent, or Firm* — Holtz, Holtz, Goodman & Chick, PC (57) ABSTRACT

A microdissection apparatus includes a laser light source to emit laser light, and a laser light irradiation optical system to irradiate a sample with the laser light from the laser light source. The laser light irradiation optical system includes an active optical element, which is allowed to form a pattern reflecting a necessary area, and sets a laser light irradiation area, to which the laser light is applied, based on the pattern formed on the active optical element.

36 Claims, 7 Drawing Sheets

MICRODISSECTION APPARATUS AND METHOD

CROSS-REFERENCE TO RELATED APPLICATIONS

This application is based upon and claims the benefit of priority from the prior Japanese Patent Applications No. 2002-317997, filed Oct. 31, 2002; and No. 2003-341157, filed Sep. 30, 2003, the entire contents of both of which are incorporated herein by reference.

BACKGROUND OF THE INVENTION

1. Field of the Invention

The present invention relates to a microdissection apparatus and method for microdissecting a biological sample.

2. Description of the Related Art

In recent years, in a field of research of, e.g., genes, a technique to take out only a target cell from a biological sample section is very important to perform a DNA analysis or the like about a specific cell of the biological sample section.

As an apparatus used to cut a necessary cell from a biological sample section under a microscope, a microdissection apparatus adopting a method to collect a necessary area in a sample such as described below has been conventionally proposed.

U.S. Pat. No. 5,998,129 discloses a method by which a sample is fixed on a sample fixing base (slide glass) having a film attached thereto, a necessary area is cut with the film by tracing a contour of the necessary area on the sample with a focused beam of UV laser light transmitted through an objective lens while moving the sample by an electric stage, the cut area is then irradiated with a defocused beam of UV laser light and flipped, the cut sample area is attached to a sample collection adhesive cap arranged above the sample, and it is then collected.

U.S. Pat. No. 6,215,550B1 discloses a method by which a sample collection adhesive cap having an adhesive film, which bonds only an area irradiated with IR laser light, is mounted on a sample, a necessary area on the sample is irradiated with the IR laser light, and the necessary area is collected by bonding only the necessary area on the sample to the adhesive film surface.

A specification of U.S. Patent Application Publication No. 2002/0048747A1 discloses a method by which a sample is fixed on a sample fixing base (slide glass) having a film attached thereto, a sample fixing surface of the sample fixing base is faced downwards, a necessary area on the sample is cut with the film by tracing a contour of the necessary area with UV laser light transmitted through an objective lens from an upper part of the sample fixing base, and the cut sample area is collected by dropping it into a sample collection tube arranged below the sample.

These methods are constituted by a technique to cut a necessary area of a sample under a microscope and a technique to collect the cut area.

Further, in these methods, to trace a contour of a necessary area on a sample with laser light or scan a beam of laser light on an entire necessary area of a sample, there has been put into practical use an apparatus that uses, e.g., an electric XY stage with step motors for moving a sample side with respect to a fixed beam of laser light, or an apparatus that uses, e.g., a laser light beam scanning mechanism with galvano mirrors for scanning a beam of laser light with respect to a fixed sample.

As disclosed in these cited references, in apparatuses adopting the method to trace a contour of a necessary area on a sample with laser light or a method to irradiate an entire necessary area with laser light, since the laser light is applied to the sample while changing a relative position between the beam of laser light and the sample, i.e., since the stage side or the laser light side must be moved, an operation to trace the contour of the necessary area with the laser light requires a considerable time when many necessary areas are scattered on the sample.

Furthermore, when cutting a necessary area by irradiating it with laser light to trace a contour of the necessary area on a sample, the sample tends to be deformed in the middle of dissection resulting from a pressure generated by evaporation of the sample itself or a stress at an uncut part, it is hard to correctly cut the necessary area if the sample is particularly a deformable biological sample. Therefore, when the necessary area is small, not only the necessary area cannot be correctly collected, but also a large amount of impurities may be sometimes mixed, and there occurs a problem that the accuracy of the subsequent analysis of the sample is greatly affected.

BRIEF SUMMARY OF THE INVENTION

According to one aspect of the present invention, the present invention is directed to a microdissection apparatus used to obtain a necessary area from a sample. The microdissection apparatus according to the present invention comprises a laser light source to emit laser light; and a laser light irradiation optical system to irradiate the sample with the laser light from the laser light source. The laser light irradiation optical system includes an active optical element, which is allowed to form a pattern reflecting the necessary area. The laser light irradiation optical system sets a laser light irradiation area, to which the laser light is applied, based on the pattern formed on the active optical element.

In another aspect, the present invention is directed to a microdissection method used to obtain a necessary area from a sample. The microdissection method according to the present invention irradiates the sample with laser light through an active optical element, which is allowed to form a pattern reflecting the necessary area.

Additional advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Embodiments according to the present invention will now be described hereinafter with reference to the accompanying drawings.

First Embodiment

Figure 1:
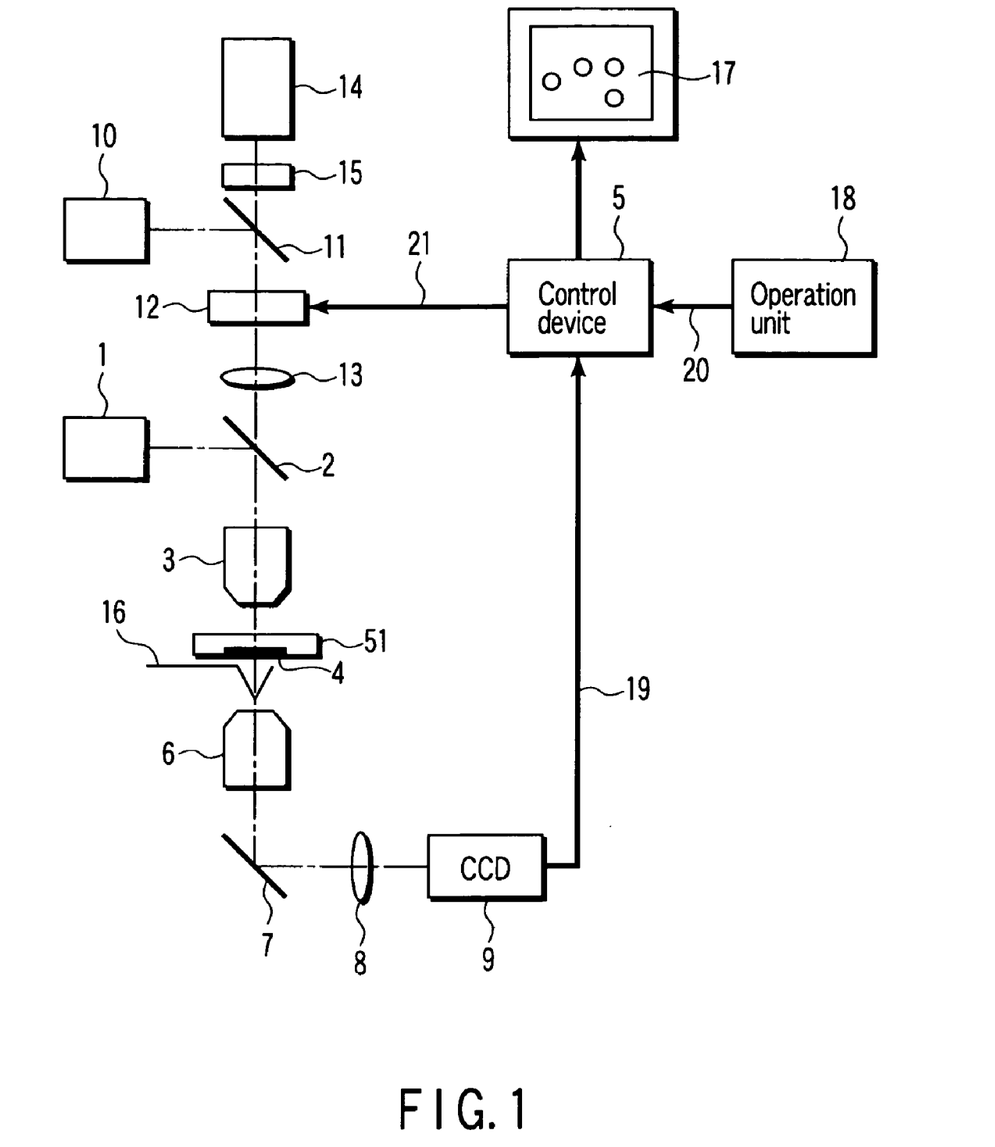
FIG. 1 shows a schematic structure of a microdissection apparatus according to a first embodiment of the present invention.

FIG. 1 shows a schematic structure of a microdissection apparatus using an inverted microscope to which the present invention is applied.

In FIG. 1, a sample 4 is fixed on a sample holder, e.g., a surface of a slide glass 51. The slide glass 51 is mounted on an XY stage, which is electrically or manually driven although not shown, and an arbitrary position of the sample 4 can be observed through a microscope.

The microdissection apparatus further includes a laser light source 14, which emits laser light, and a laser light irradiation optical system, which irradiates the sample 4 with the laser light from the laser light source 14. The laser light irradiation optical system includes a collimator lens 15, an active optical element 12, a relay lens 13, and an objective lens 3 for the laser light. The active optical element 12 is a transmission type active optical element. Although not restricted, the transmission type active optical element 12 is constituted by, e.g., a transmission type liquid crystal substrate.

The laser light source 14 emits UV laser light having a predetermined wavelength. The collimator lens 15 expands a beam diameter of the laser light emitted from the laser light source 14.

A beam of laser light emitted from the laser light source 14 is expanded by the collimator lens 15 to a diameter that is allowed to illuminate substantially a whole of the transmission type liquid crystal substrate 12. The laser light transmitted through the collimator lens 15 is led to the transmission type liquid crystal substrate 12. The laser light transmitted through a pattern of the transmission type liquid crystal substrate 12 passes through the relay lens 13 and the objective lens 3, and the sample 4 is irradiated with the laser light.

The sample 4 is evaporated and cut by applying the laser light through the pattern. Moreover, a part cut from the sample 4 is dropped into a sample collection tube 16 and collected.

The microdissection apparatus further has an observation optical system, which acquires an observation image of the sample 4, and an illumination optical system, which illuminates the sample 4 for observation. The illumination optical system includes a light source 1 for sample observation, a half mirror 2, and an objective lens 3 for the laser light. The observation optical system includes an objective lens 6 for observation, a reflection mirror 7, an image forming lens 8, and an imaging element 9 as imaging means. Although not restricted, the imaging element 9 is constituted by, e.g., a CCD camera.

The light emitted from the light source 1 for sample observation is reflected by the half mirror 2 and transmitted through the objective lens 3 for the laser light to illuminate the sample 4.

The objective lens 6 is arranged below the slide glass 51. The light that has been transmitted through the sample 4 enters the objective lens 6. Moreover, the light that has entered the objective lens 6 is reflected by the reflection mirror 7, transmitted through the image forming lens 8 and image-formed on an imaging surface of the CCD camera 9.

The microdissection apparatus further includes a pattern image projection optical system, which projects an image of a pattern formed on the transmission type liquid crystal substrate 12 onto the sample 4. The pattern image projection optical system includes a light source 10 for pattern image projection, a half mirror 11, a transmission type liquid crystal substrate 12, a relay lens 13 and an objective lens 3.

The light emitted from the light source 10 for pattern image projection is reflected by the half mirror 11, and led to the transmission type liquid crystal substrate 12, which is a transmission type active optical element as an active optical element.

The transmission type liquid crystal substrate 12 forms a pattern (laser light irradiation area) with a high resolution, which sets a cut area on the sample 4, and transmits the light from the light source 10 in accordance with this pattern.

Additionally, the light (pattern image) transmitted through the transmission type liquid crystal substrate 12 is transmitted through the relay lens 13, the half mirror 2, and the objective lens 3 for the laser light, then reduced and projected onto the sample 4. Further, the pattern image transmitted through the sample 4 passes through the objective lens 6, is reflected by the reflection mirror 7, transmitted through the image forming lens 8 and image-formed on the imaging surface of the CCD camera 9.

Although the half mirror 2 and the half mirror 11 are arranged on the optical path of the laser light, it is good to remove them from the optical path when irradiating the sample 4 with the laser light from the laser light source 14. By doing so, the laser light is no longer absorbed by the half mirror 2 and the half mirror 11, and the power of the laser light can be effectively utilized.

A control device 5 as controller is connected to the CCD camera 9. Besides the above-described transmission type liquid crystal substrate 12, to the control device 5 are connected a monitor 17 as displaying means and an operation unit 18 as inputting means.

In the operation unit 18, a mouse, a joy stick or the like is used.

The control device 5 fetches an image signal 19 outputted from the CCD camera 9, and displays it in the monitor 17. Furthermore, the control device 5 moves a cursor on the monitor 17 by using operation information 20 according to an operation of the mouse or the joy stick, and sets a pattern expressing an (necessary) area on the sample 4 to be collected by moving the cursor. Moreover, the control device 5 outputs a control signal 21 to the transmission type liquid crystal substrate 12, and projects onto the transmission type liquid crystal substrate 12 the pattern expressing the cut area on the sample 4 that is set in the monitor 17.

An operation of the thus configured embodiment will now be described.

First, the sample 4 is fixed on the slide glass 51. Then, the slide glass 51 is mounted on the XY stage.

Subsequently, the light source 1 for sample observation is turned on. The light emitted from the light source 1 is reflected by the half mirror 2 and transmitted through the objective lens 3 for the laser light to illuminate the sample 4. The light transmitted through the sample 4 passes through the objective lens 6, is reflected by the reflection mirror 7, transmitted through the image forming lens 8 and image-formed on the imaging surface of the CCD camera 9. Then, an observation image of the sample 4 imaged by the CCD camera 9 is supplied to the control device 5 as an image signal 19, and displayed in the monitor 17.

Figure 2A:
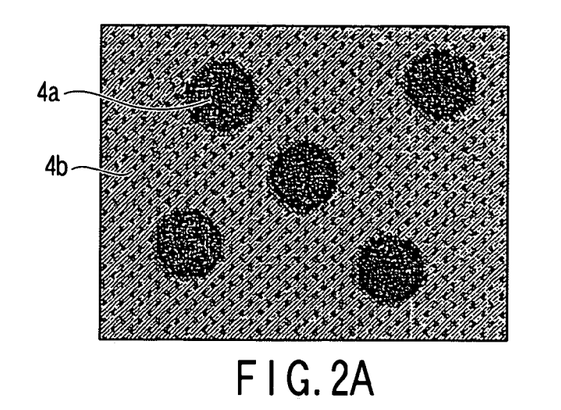
FIG. 2A shows an observation image of a sample displayed in a monitor.

FIG. 2A shows an observation image of the sample displayed in the monitor 17. Here, it is assumed that 4a is an area on the sample 4 to be collected for analysis and 4b is any other unnecessary area. Here, the area 4a to be collected matches with an area required for analysis.

An operator operates the mouse or the joy stick in the operation unit 18 while watching a screen of the observation image in the monitor 17, moves the cursor in the monitor 17, and traces a boundary between the area 4a on the sample 4 to be collected and any other area 4b, i.e., a contour of the area 4a to be collected.

Then, a pattern representing the area 4a on the sample 4 to be collected is set in the monitor 17. Information of this pattern is supplied to the transmission type liquid crystal substrate 12 as a control signal 21 by the control device 5. Therefore, is on the transmission liquid crystal substrate 12, a pattern (laser light irradiation area) reflecting the area 4a on the sample 4 to be collected that is set in the monitor 17 is formed, i.e., projected.

Then, the light source 10 for pattern image projection is turned on, and the brightness of the light source 1 for sample observation is lowered.

The light emitted from the light source 10 is reflected by the half mirror 11, led to the transmission type liquid crystal substrate 12, transmitted through the pattern part projected on the transmission type liquid crystal substrate 12.

The light (pattern image) transmitted through the transmission type liquid crystal substrate 12 is transmitted through the relay lens 13, the half mirror 2 and the objective lens 3 for the laser light, and reduced and projected onto the sample 4. The pattern image transmitted through the sample 4 passes through the objective lens 6, is reflected by the reflection mirror 7, transmitted through the image forming lens 8, and image-formed on the imaging surface of the CCD camera 9.

Then, the pattern image imaged by the CCD camera 9 is supplied to the control device 5 as an image signal 19 and displayed in the monitor 17. Here, since the brightness of the light source 1 for sample observation is reduced, the pattern image in the monitor 17 is clearly displayed.

Figure 2B:
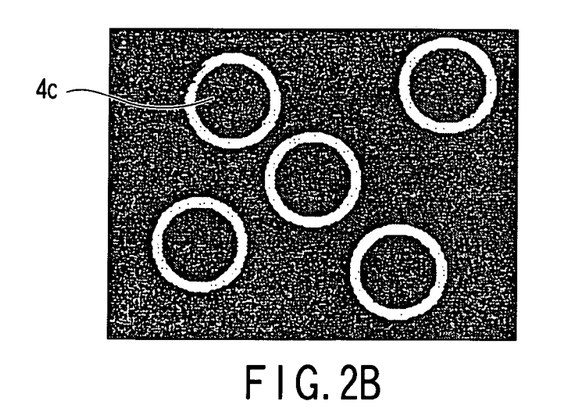
FIG. 2B shows a pattern image displayed in the monitor.

FIG. 2B shows a pattern image displayed in the monitor 17. Here, 4c denotes a pattern image used to transmit the laser light.

An operator judges whether it is a pattern shape optimum to be collect the area 4a on the sample 4 by making reference to a shape of the pattern image 4c in the monitor 17.

On this stage, the shape of the pattern image 4c can be corrected by operating the operation unit 18 and moving the cursor in the monitor 17, if necessary.

When the pattern shape is determined, the laser light source 14 is turned on.

A beam of laser light emitted from the laser light source 14 is expanded to a diameter that is allowed to illuminate substantially a whole of the transmission type liquid crystal substrate 12 by the collimator lens 15, and then led to the transmission type liquid crystal substrate 12.

The laser light transmitted through the pattern of the transmission type liquid crystal substrate 12 passes through the relay lens 13 and the objective lens 3, and the sample 4 is irradiated with the laser light. Therefore, the part of the sample 4 along the pattern shape irradiated with the laser light is evaporated, and the area 4a to be collected is cut away.

Figure 2C:
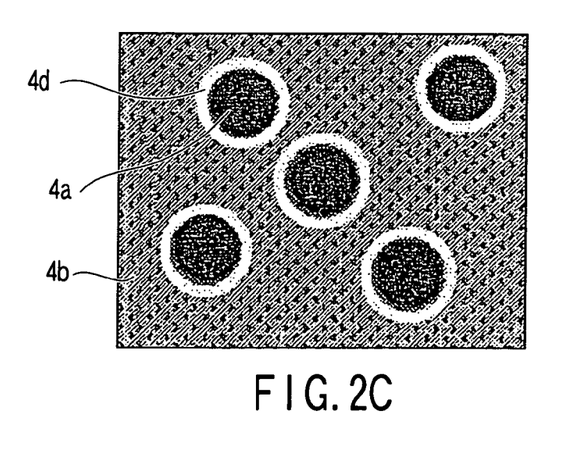
FIG. 2C shows an observation image of a sample from which an area to be collected is cut.

Then, when the light source 10 for pattern image projection is turned off and the brightness of the light source 1 for sample observation is restored, the observation image of the sample 4 is again displayed in the monitor 17. FIG. 2C shows an observation image of the sample 4 in a state that the area 4a is cut away. Here, 4a denotes an area on the sample to be collected for analysis; 4b, any other unnecessary area; and 4d, a sample removed portion evaporated by irradiation of the laser light along the pattern shape.

Then, the area 4a cut from the sample 4 is pushed into the sample collection tube 16 and collected.

Incidentally, as a method of collecting the area 4a cut from the sample 4, it is possible to adopt, e.g., the methods disclosed in U.S. Pat. No. 5,998,129 and the specification of U.S. Patent Application Publication No. 2002/0048747A1 as well as a method disclosed in a specification of Jpn. Pat. Appln. KOKAI Publication No. 2002-14643 precedently filed by the present applicant.

Therefore, as described above, contours of a plurality of necessary areas on an observation image of the sample 4 are traced, each area is set, a laser light irradiation area is set for each of these necessary areas by the transmission type liquid crystal substrate 12, and these areas are irradiated with the laser light. Therefore, these areas can be cut at a time. As compared with a conventional apparatus that a contour of each of a plurality of necessary areas on the sample is cut by irradiating it with the laser light while changing the relative position of the laser light and the sample, the operation to cut the necessary area on the sample can be easily and efficiently performed, thereby greatly reducing the operation time.

Further, the laser light irradiation area set on the sample 4 by the transmission type liquid crystal substrate 12 can be cut by only irradiating it with the laser light. Therefore, as compared with a conventional apparatus that cannot correctly cut the necessary area on the sample when the necessary area on the sample is small and the sample deviates in the middle of tracing the contour, the apparatus according to this embodiment can correctly cut the area even if the necessary area is small. Therefore, impurities are not mixed in the middle of dissection, and the subsequent analysis of the sample can be effected with the high accuracy.

First Modification

Figure 3:
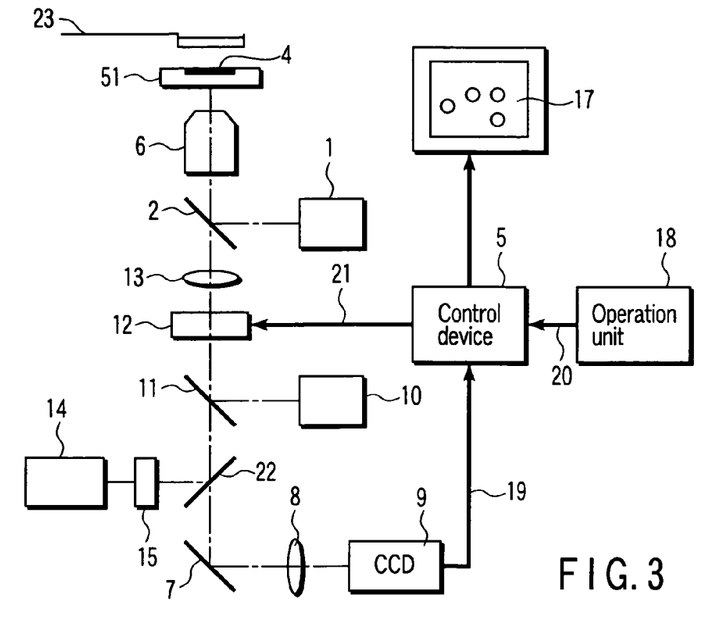
FIG. 3 shows a schematic structure of a microdissection apparatus according to a first modification of the first embodiment.

Although the optical system for laser irradiation which has the objective lens 3 for the laser light and the optical system for observation which has the objective lens 6 for observation are separately prepared in the first embodiment, whereas the first modification has a structure that the optical system for laser light irradiation and the optical system for observation are shared as shown in FIG. 3 in which like reference numerals denote parts equal to those in FIG. 1.

In this structure, the laser light irradiation optical system includes a collimator lens 15, a half mirror 22, a transmission type liquid crystal substrate 12, a relay lens 13, and an objective lens 6 for observation. The illumination optical system includes a light source 1 for sample observation, a half mirror 2, and an objective lens 6 for observation. The observation optical system includes an objective lens 6 for observation, a relay lens 13, a transmission type liquid crystal substrate 12, a reflection mirror 7, an image forming lens 8 and a CCD camera 9. The pattern image projection optical system includes a light source 10 for pattern image projection, a half mirror 11, a transmission type liquid crystal substrate 12, a relay lens 13, and an objective lens 6 for observation.

The light emitted from the light source 1 for sample observation is reflected by the half mirror 2 and transmitted through the objective lens 6 to illuminate the sample 4. The light reflected by the sample 4 is transmitted through the objective lens 6, the half mirror 2, the relay lens 13, the transmission type liquid crystal substrate 12, and the half mirrors 11 and 12, reflected by the reflection mirror 7, transmitted through the image forming lens 8, and image-formed on an imaging surface of the CCD camera 9.

Furthermore, the light emitted from the light source 10 for pattern image projection is reflected by the half mirror 11, transmitted through the transmission type liquid crystal substrate 12, the relay lens 13 and the objective lens 6 to illuminate the sample 4. The light reflected by the sample 4 passes through the same optical path as that of the light emitted from the light source 1, and image-formed on the imaging surface of the CCD camera 9.

Moreover, the laser light emitted from the laser light source 14 is transmitted through the collimator lens 15, reflected by the half mirror 22, and transmitted through the transmission type liquid crystal substrate 12, the relay lens 13 and the objective lens 6, and the sample 4 is irradiated with this laser light.

It is to be noted that the area cut from the sample 4 is collected by the method disclosed in U.S. Pat. No. 6,215, 550B1 mentioned above by using a sample collection adhesive cap in the first modification.

Even if such a structure is adopted, the same advantage as that of the first embodiment can be expected. Additionally, since the objective lenses for observation and for the laser light can be shared, the structure can be simplified.

Second Modification

Figure 4:
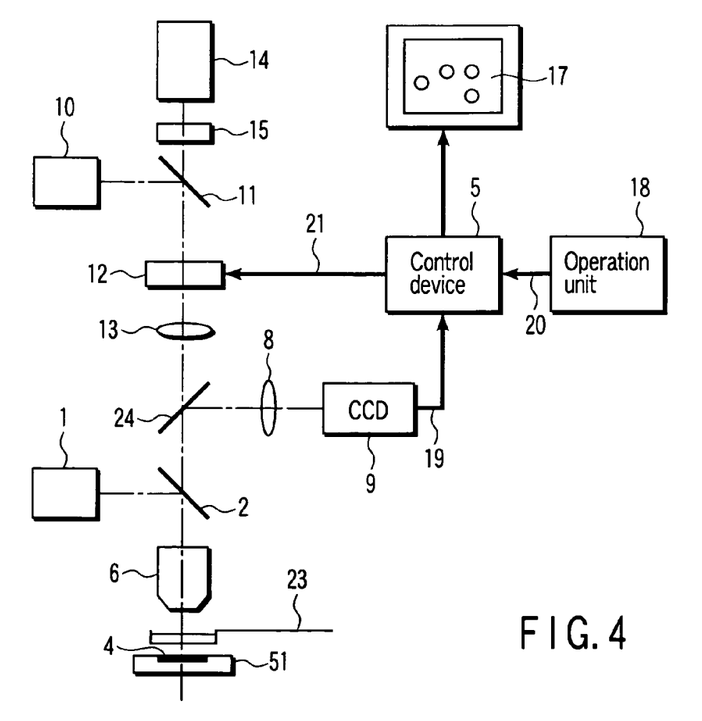
FIG. 4 shows a schematic structure of a microdissection apparatus according to a second modification of the first embodiment.

Although the microdissection apparatus using the inverted microscope has been described in the first embodiment, the second modification can be also applied to, e.g., a microdissection apparatus using an erecting microscope as shown in FIG. 4 in which like reference numerals denote parts equal to those in FIG. 4.

In this structure, the laser light irradiation optical system includes a collimator lens 15, a transmission type liquid crystal substrate 12, a relay lens 13, and an objective lens 6 for observation. The illumination optical system includes a light source 1 for sample observation, a half mirror 2, and an objective lens 6 for observation. The observation optical system includes an objective lens 6 for observation, a half mirror 24, an image forming lens 8, and a CCD camera 9. The pattern image projection optical system includes a light source 10 for pattern image projection, a half mirror 11, a transmission type liquid crystal substrate 12, a relay lens 13, and an objective lens 6 for observation.

The light emitted from the light source 1 for sample observation is reflected by the half mirror 2 and transmitted through the objective lens 6 to illuminate the sample 4. The light reflected by the sample 4 is transmitted through the objective lens 6 and the half mirror 2, reflected by the half mirror 24, transmitted through the image forming lens 8, and image-formed on an imaging surface of the CCD camera 9.

Further, the light emitted from the light source 10 for pattern image projection is reflected by the half mirror 11 and transmitted through the transmission type liquid crystal substrate 12, the relay lens 13 and the objective lens 6 to illuminate the sample 4. The light reflected by the sample 4 passes through the same optical path as that of the light emitted from the light source 1, and image-formed on the imaging surface of the CCD camera 9.

Furthermore, the laser light emitted from the laser light source 14 is transmitted through the collimator lens 15, the transmission type liquid crystal substrate 12, the relay lens 13 and the objective lens 6, and the sample 4 is irradiated with the laser light.

It is to be noted that the area cut from the sample 4 is also collected by the method disclosed in U.S. Pat. No. 6,215, 550B1 mentioned above using a sample collection adhesive cap in the second modification.

Even if such a structure is adopted, the same advantage as that of the first embodiment can be expected.

Third Modification

In the first embodiment, an operator operates the mouse or the joy stick in the operation unit 18 and forms in the monitor 17 a pattern representing an area to be collected while watching an observation image of the sample 4 in the monitor 17. However, if a judgment condition of a necessary portion and an unnecessary portion on the sample 4 can be formulated, the pattern expressing the area on the sample 4 to be collected can be automatically formed from the observation image of the sample 4, and the pattern representing the area on the sample 4 to be collected can be also automatically projected onto the transmission type liquid crystal substrate 12 by using this pattern information.

Since an operation by the operator to select the area while watching the observation image can be eliminated by doing so, simplification of the operation and a great reduction in the operation time can be realized.

Second Embodiment

A second embodiment according to the present invention will now be described.

Figure 5:
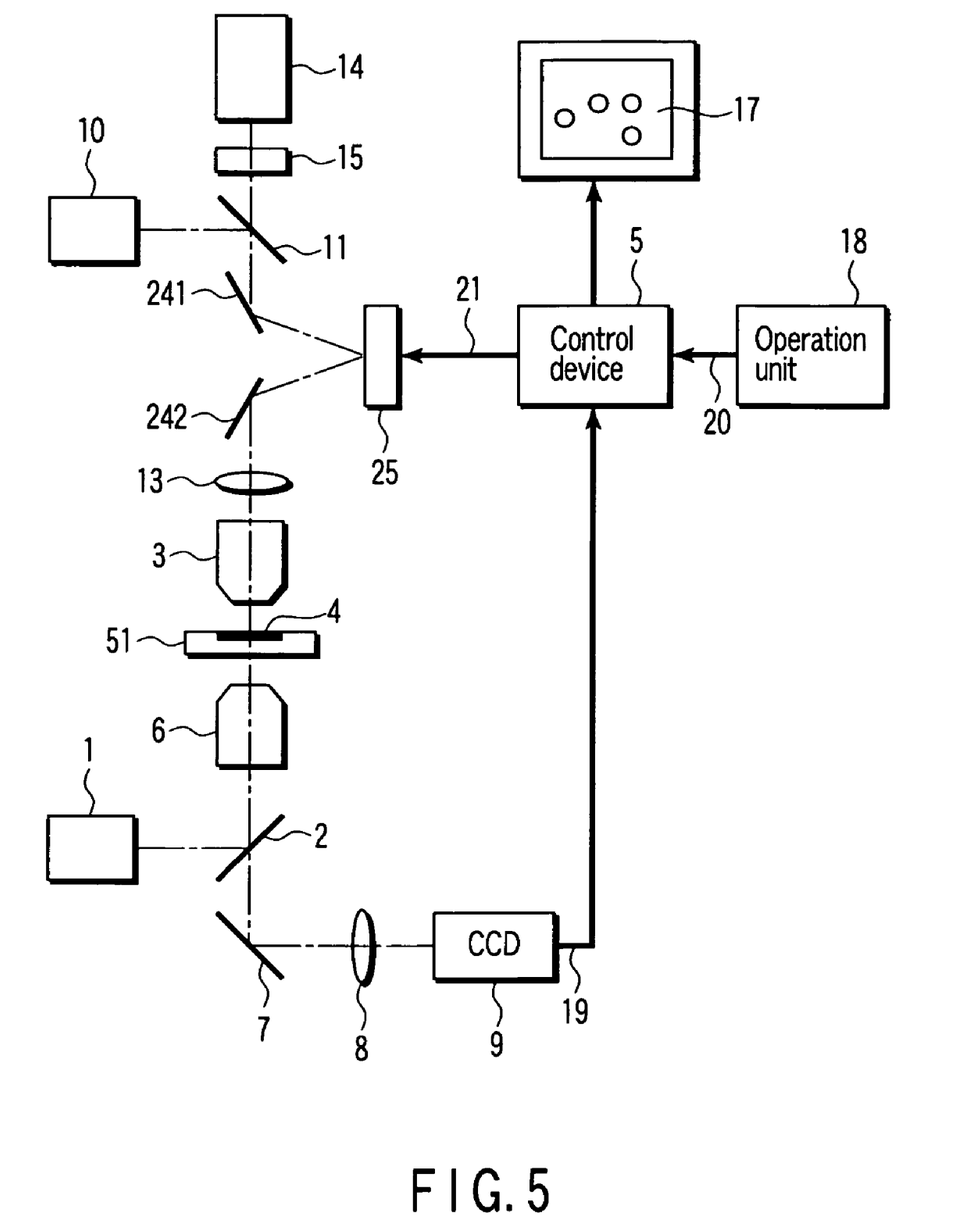
FIG. 5 shows a schematic structure of a microdissection apparatus according to a second embodiment of the present invention.

FIG. 5 shows a schematic structure of a microdissection apparatus using an inverted microscope to which the present invention is applied, and like reference numerals denote parts equal to those in FIG. 1.

In this embodiment, a laser light irradiation optical system includes a collimator lens 15, a reflection mirror 241, an active optical element 25, a reflection mirror 242, a relay lens 13, and an objective lens 3 for the laser light. The active optical element 25 is a reflection type active optical element. Although not restricted, the reflection type active optical element 25 is constituted by, e.g., a transmission type liquid crystal substrate. Although not restricted, the reflection type active optical element 25 is constituted by, e.g., a micro mirror array.

The micro mirror array 25 has many small mirrors, which are two-dimensionally arranged. One small mirror has a dimension that is approximately 16 µm×16 µm and corresponds to one pixel. A plurality of small mirrors can be respectively operated to rotate at a predetermined tilt angle by an electrostatic electric field effect. By controlling a tilt angle of the small mirror corresponding to each pixel based on a control-signal 21 from a control device 5, a reflection pattern (laser light irradiation area) representing a cut area on the sample 4 can be formed.

An illumination optical system includes a light source 1 for sample observation, a half mirror 2, and an objective lens 6 for observation. An observation optical system includes an objective lens 6 for observation, a reflection mirror 7, an image forming lens 8 and a CCD camera 9. A pattern image projection optical system includes a light source 10 for pattern image projection, a half mirror 11, a reflection mirror 241, a micro mirror array 25, a reflection mirror 242, a relay lens 13, and an objective lens 3 for the laser light.

The light emitted from the light source 1 for sample observation is reflected by the half mirror 2 and transmitted through the objective lens 6 for observation to illuminate the sample 4. The light reflected by the sample 4 enters the objective lens 6, is transmitted through the half mirror 2, reflected by the reflection mirror 7, transmitted through the image forming lens 8, and image-formed on an imaging surface of the CCD camera 9.

Further, the light emitted from the light source 10 for pattern image projection is reflected by the half mirror 11 and the reflection mirror 241, and led to the micro mirror array 25. A reflection pattern (laser light irradiation area) which sets a cut area on the sample 4 is formed on the micro mirror array 25 based on a control signal 21 from the control device 5. The micro mirror array 25 reflects the light from the light source 10 in accordance with this reflection pattern.

The light (pattern image) reflected by the micro mirror array 25 is reflected by the reflection mirror 242, transmitted through the relay lens 13 and the objective lens 3 for the laser light, and reduced and projected onto the sample 4. Furthermore, the pattern image transmitted through the sample 4 passes through the objective lens 6 and the half mirror 2, is reflected by the reflection mirror 7, transmitted through the image forming lens 8, and image-formed on the imaging surface of the CCD camera 9.

Moreover, a beam of laser light from the laser light source 14 is expanded by the collimator lens 15 to a diameter that is allowed to illuminate substantially a whole of the micro mirror array 25. The laser light transmitted through the collimator lens 15 is led to the micro mirror array 25 through the reflection mirror 241. A reflection pattern (laser light irradiation area) which sets a cut area on the sample 4 is formed on the micro mirror array 25 based on a control signal 21 from the control device 5. The micro mirror array 25 reflects the light from the light source 10 in accordance with this reflection pattern.

The laser light reflected by the reflection pattern of the micro mirror array 25 is reflected by the reflection mirror 242 and transmitted through the relay lens 13 and the objective lens 3, and the sample 4 is irradiated with the laser light. The sample 4 is evaporated and cut by applying the laser light through the pattern.

Any other structure is the same as that in FIG. 1.

In such a structure, the sample 4 is first fixed to the slide glass 51. Then, the slide glass 51 is mounted on the XY stage.

Subsequently, the light source 1 for sample observation is turned on. The light emitted from the light source 1 is reflected by the half mirror 2 and transmitted through the objective lens 6 to illuminate the sample 4. The light reflected by the sample 4 is transmitted through the objective lens 6, reflected by the reflection mirror 7, transmitted through the image forming lens 8, and image-formed on the image forming surface of the CCD camera 9. Further, an observation image of the sample 4 imaged by the CCD camera 9 is supplied to the control device 5 as an image signal 19, and displayed in the monitor 17.

Here, the area 4a on the sample 4 to be collected and any other unnecessary area 4b are displayed on the monitor 17 as the observation image of the sample 4 as shown in FIG. 2A. Here, the area 4a to be collected matches with the area required for analysis.

An operator operates the mouse or the joy stick in the operation unit 18 and moves the cursor on the monitor 17 while watching a screen of the observation image on the monitor 17, and traces a boundary between the area 4a on the sample 4 to be collected and any other area 4b, i.e., a contour of the area 4a to be collected.

Then, a pattern representing the area 4a on the sample 4 to be collected is set on the monitor 17. Information of this pattern is supplied to the micro mirror array 25 as a control signal 21 by the control device 5. Therefore, a reflection pattern (laser light irradiation area) that is formed in the monitor 17 and represents the area 4a on the sample 4 to be collected is set on the micro mirror array 25.

In this state, the light source 10 for pattern image projection is turned on, and the brightness of the light source 1 for sample observation is lowered.

The light emitted from the light source 10 is reflected by the half mirror 11 and the reflection mirror 241 and led to the micro mirror array 25, and the light reflected on the micro mirror array 25 (pattern image) is reflected by the reflection mirror 242, transmitted through the relay lens 13, the objective lens 3 for the laser light, and reduced and projected onto the sample 4. Further, the pattern image transmitted through the sample 4 is transmitted through the objective lens 6, reflected by the reflection mirror 7, transmitted through the image forming lens 8, and image-formed on the imaging surface of the CCD camera 9.

Then, the pattern image imaged by the CCD camera 9 is supplied to the control device 5 as an image signal 19, and displayed in the monitor 17. In this case, since the brightness of the light source 1 for sample observation is decreased, the pattern image on the monitor 17 is clearly displayed.

Here, the pattern image 4c used to transmit the laser light is displayed as a pattern image in the monitor 17 as shown in FIG. 2B.

An operator judges whether it has a pattern shape optimum for collecting the area 4a on the sample 4 by making reference to a shape of the pattern image 4c in the monitor 17.

On this stage, the shape of the pattern image 4c can be corrected by operating the operation unit 18 and moving the cursor in the monitor 17 if necessary.

When the pattern shape is determined, the laser light source 14 is turned on.

A beam of laser light emitted from the laser light source 14 is expanded to a diameter that is allowed to illuminate substantially a whole of the micro mirror array 25 by the collimator lens 15, and then led to the micro mirror array 25 through the reflection mirror 241.

The laser light reflected with the reflection pattern of the micro mirror array 25 is reflected by the reflection mirror 242 and transmitted through the objective lens 3, and the sample 4 is irradiated with the laser light. Therefore, the part of the sample 4 along the pattern shape irradiated with the laser light is evaporated, and the area 4a to be collected is cut away.

Then, when the light source 10 for pattern image projection is turned off and the brightness of the light source 1 for sample observation is restored, the observation image of the sample 4 is again displayed in the monitor 17.

Here, as the observation image of the sample 4 with the area 4a being cut away, there are displayed the area 4a on the sample 4 to be collected for analysis, any other unnecessary area 4b, and a sample removed portion 4d evaporated by irradiation of the laser light along the pattern shape as shown in FIG. 2C.

Then, the area 4a cut from the sample 4 is dropped into a non-illustrated sample collection tube and collected.

In this case, likewise, as methods for collecting the area 4a cut from the sample 4, it is possible to adopt methods disclosed in U.S. Pat. No. 5,998,129 and the specification of U.S. Patent Application Publication No. 2002/0048747A1 mentioned above as well as a method disclosed in the specification of Jpn. Pat. Appln. KOKAI. Publication No. 2002/14643 precedently filed by the present applicant.

Therefore, as described above, contours of a plurality of required areas of the sample 4 on the observation image are traced, the respective areas are specified, these required areas are set on the sample 4 through the micro mirror array 25, and the laser light is irradiated. Therefore, these areas are cut away at a time. Therefore, the same advantages as those in the first embodiment can be expected.

Furthermore, since the losses of the UV laser light can be reduced by using the micro mirror array 25 as compared with a case using the transmission type liquid crystal substrate 12 described in connection with the first embodiment, cutting of the required area can be efficiently performed.

Modification

Figure 6:
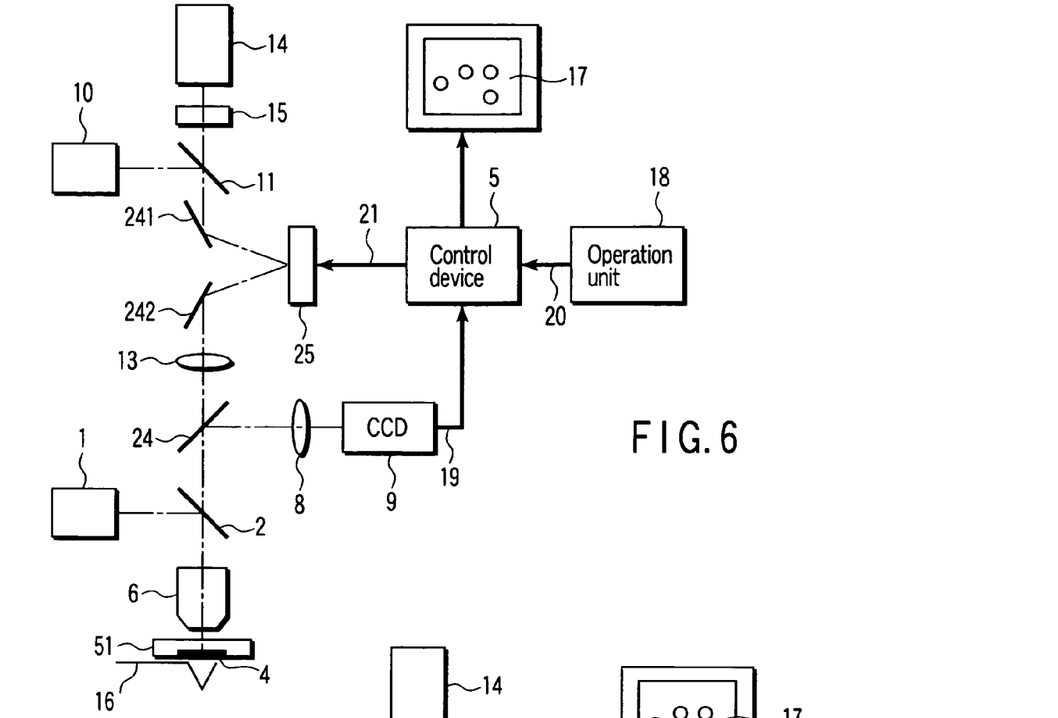
FIG. 6 shows a schematic structure of a microdissection apparatus according to a modification of the second embodiment.

Although the microdissection apparatus using the inverted microscope has been described in the first embodiment, the present invention can be applied to a microdissection apparatus using an erecting microscope in this modification as shown in FIG. 6 in which like reference numerals denote parts equal to those in FIG. 1.

In this structure, the laser light irradiation optical system includes a collimator lens 15, a reflection mirror 241, a micro mirror array 25, a reflection mirror 242, a relay lens 13, and an objective lens 6 for observation. An illumination optical system includes a light source 1 for sample observation, a half mirror 2, and an objective lens 6 for observation. An observation optical system includes an objective lens 6 for observation, a half mirror 24, an image forming lens 8, and a CCD camera 9. A pattern image projection optical system includes a light source 10 for pattern image projection, a half mirror 11, a reflection mirror 241, a micro mirror array 25, a reflection mirror 242, a relay lens 13, and an objective lens 3 for the laser light.

The light emitted from the light source 1 for sample observation is reflected by the half mirror 2 and transmitted through the objective lens 6 to illuminate the sample 4. The light reflected by the sample 4 is transmitted through the half mirror 2, reflected by the half mirror 24, transmitted through the image forming lens 8, and image-formed on an imaging surface of the CCD camera 9.

Furthermore, the light emitted from the light source 10 for pattern image projection is reflected by the half mirror 11 and the reflection mirror 241, and led to the micro mirror array 25. The light (pattern image) reflected with the reflection pattern of the micro mirror array 25 is reflected by the reflection mirror 242 and transmitted through the relay lens 13, the half mirrors 24 and 2 and the objective lens 6 to illuminate the sample 4. The light reflected by the sample 4 passes through the same optical path as that of the light emitted from the light source 1, and image-formed on the imaging surface of the CCD camera 9.

Moreover, the laser light emitted from the laser light source 14 is transmitted through the collimator lens 15, reflected by the reflection mirror 241, and led to the micro mirror array 25. The light (pattern image) reflected with the reflection pattern of the micro mirror array 25 is reflected by the reflection mirror 242 and transmitted through the relay lens 13 and the objective lens 6 to illuminate the sample 4.

It is to be noted that the area cut from the sample 4 is dropped into the sample collection tube 16 and collected in the second modification.

By doing so, the same advantages as those in the second embodiment can be expected.

Third Embodiment

The third embodiment according to the present invention will now be described.

This embodiment is a microdissection apparatus, which destroys DNA at a part of a sample, which is not required for DNA analysis by selectively irradiating the sample with the laser light in accordance with a pattern formed on an active optical element.

Figure 7:
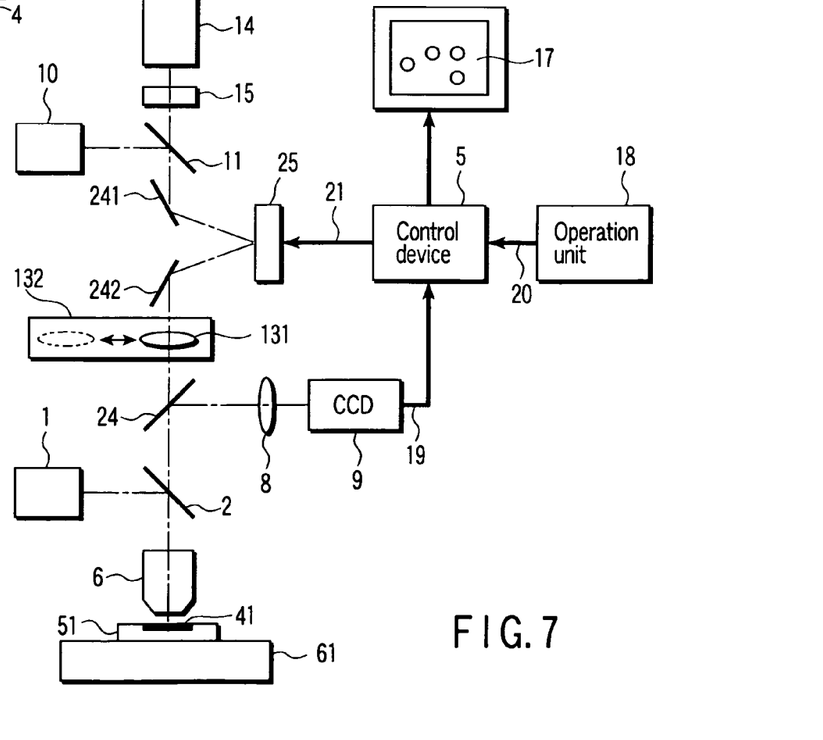
FIG. 7 shows a schematic structure of a microdissection apparatus according to a third embodiment of the present invention.

FIG. 7 shows a schematic structure of an erecting microscope type micro dissection apparatus using a reflection type active optical element according to the third embodiment of the present invention. In FIG. 7, like reference numerals denotes members equivalent to those in FIG. 6.

The microdissection apparatus according to this embodiment basically has an apparatus structure in which a relay lens can be attached/detached to/from an optical path of the laser light for the apparatus shown in FIG. 6 (modification of the second embodiment).

Since the apparatus structure of the microdissection apparatus according to this embodiment is substantially the same as the apparatus according to the modification of the second embodiment, a description will be given attaching importance mainly to different parts.

In FIG. 7, a sample 41 is fixed to a slide glass 51 as a sample holder. The slide glass 51 is mounted on the XY stage 61, which is electrically or manually driven.

In the microdissection apparatus according to this embodiment, the laser light irradiation optical system includes a collimator lens 15, a reflection mirror 241, a micro mirror array 25, a reflection mirror 242, an objective lens 6 and a relay lens 131 as well as a relay lens attachment/detachment mechanism 132 which attaches/detaches the relay lens 131 to/from an optical path.

The relay lens attachment/detachment mechanism 132 movably supports the relay lens 131, and can attach/detach the relay lens 131 to/from the optical path of the laser light between the micro mirror array 25 and the objective lens 6. That is, the relay lens attachment/detachment mechanism 132 can arrange the relay lens 131 on the optical path or remove the relay lens 131 from the optical path according to needs.

The micro mirror array 25 has many two-dimensionally arranged small mirrors, and a reflection angle of the small mirror can be switched by the control device 5. Therefore, the micro mirror array 25 can form a pattern reflecting an area required for analysis of the sample 41, i.e., a reflection pattern used to set an area of the sample 41 irradiated with the laser light.

A beam of laser light emitted from the laser light source 14 enters the collimator lens 15, and converted into a substantially parallel beam having a diameter that is allowed to illuminate substantially a whole of the micro mirror array 25. A beam of laser light from the collimator lens 15 is reflected by the reflection mirror 241, and enters the micro mirror array 25. The laser light reflected by the micro mirror array 25 is reflected by the reflection mirror 242, and directed toward the objective lens 6.

Figure 8A:
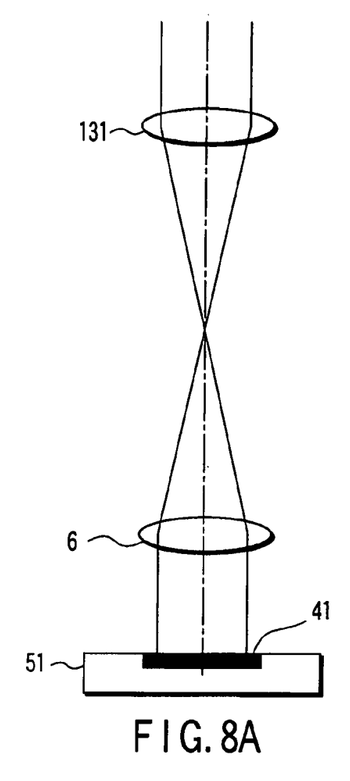
FIG. 8A shows a behavior of laser light applied to a sample in a state that a relay lens depicted in FIG. 7 is positioned on an optical path.

In a state that the relay lens 131 is positioned in the optical path, as shown in FIG. 8A, the substantially parallel beam of laser light directed toward the objective lens 6 is once converged by the relay lens 131 and then enters the objective lens 6, again converted into the substantially parallel beam by the objective lens 6, and illuminates a relatively wide range of the sample 41.

In this state, the micro mirror array 25 forms a pattern reflecting an area required for analysis of the sample 41, i.e., a reflection pattern used to set an area of the sample 41 irradiated with the laser light.

The laser light irradiation optical system reduces and projects an image of the reflection pattern formed on the micro mirror array 25 onto the sample 41. That is, the part of the sample excluding the necessary area is selectively irradiated with the laser light in accordance with the pattern formed on the micro mirror array 25.

A projection magnification of the reflection pattern depends on the relay lens 131 and the objective lens 6. The relay lens 131 is designed to have energy that is insufficient for evaporating the sample but enough to destroy the DNA per unit area of the sample surface. Therefore, the laser light applied to the sample 41 does not have the energy density that is sufficient for evaporating the sample but has the energy density that is sufficient for destroying the DNA.

In the microdissection apparatus according to this embodiment, since it is good enough that the laser light irradiation optical system irradiates the sample 41 with the laser light only with the energy density sufficient for destroying the DNA, i.e., since it is not necessary to apply the laser light to the sample with the high energy density sufficient for evaporating the sample 41, a wider area can be irradiated with the laser light than that in the apparatus according to the modification of the second embodiment.

One small mirror of the micro mirror array 25 corresponds to one pixel of can image of the pattern formed on the micro mirror array 25 projected onto the sample 41. The micro mirror array 25 can perform the on/off control to irradiation of the laser light in units of the pattern image pixel projected onto the sample 41 by switching a reflection angle of the small mirror. That is, an area of the sample 41 that is irradiated with the laser light can be arbitrarily set.

The reflection pattern formed on the micro mirror array 25 is a pattern for applying the laser light to the part of the sample 41 excluding the area required for the DNA analysis. Therefore, in the sample 41, the DNA at the part that the laser light is applied to, i.e., the part of the sample 41 excluding the area required for the DNA analysis is destroyed.

Figure 8B:
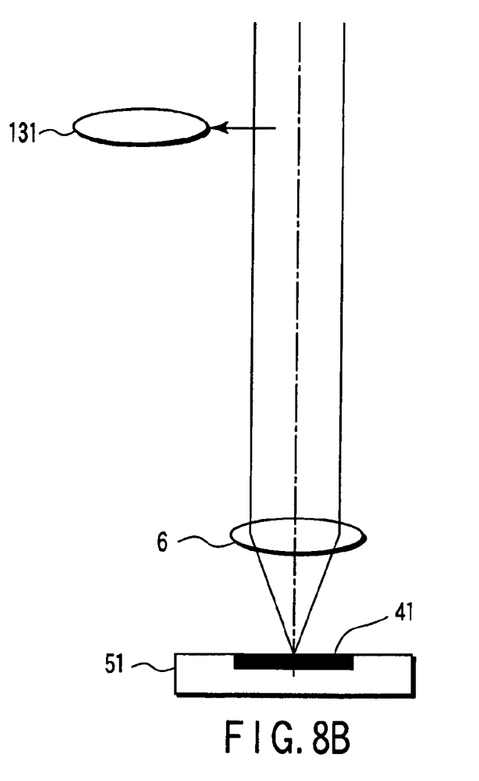
FIG. 8B shows a behavior of the laser light applied to the sample when the relay lens depicted in FIG. 7 is off the optical path.

On the other hand, in a state that the relay lens 131 is off the optical path, as shown in FIG. 8B, the substantially parallel beam of laser light directed toward the objective lens 6 enters the objective lens 6 in the form of a substantially parallel beam, converged by the objective lens 6, and illuminates a relatively narrow range of the sample 41.

In this state, the micro mirror array 25 preferably does not form a reflection pattern used to set an area of the sample 41 that is irradiated with the laser light.

The laser light, which is converged to illuminate the sample 41, has an energy that is sufficient for evaporating the sample 41 per unit area of the sample surface, i.e., the energy density that is sufficient for evaporating the sample 41.

The part of the sample 41 to which the laser light is converted and which is irradiated with the laser light is evaporated and cut.

A description will now be given as to a microdissection method using this apparatus along a general operation procedure.

The sample 41 fixed to the slide glass 51 is put on the XY stage of the microscope, and a power supply of the light source 1 for sample observation is turned on. A microscope observation image of the sample 41 illuminated by the light source 1 for sample observation is imaged to the CCD camera 9, and an image signal is displayed in the monitor through the control device 5.

Figure 9A:
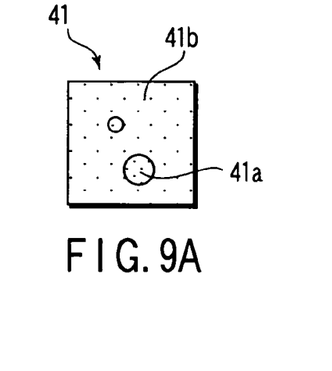
FIG. 9A shows an observation image of the sample.

FIG. 9A shows an observation image of the sample. Here, reference numeral 41a denotes a necessary area of the sample 41 to be analyzed, and reference numeral 41b designates any other unnecessary area. The necessary area 41a is, e.g., a tumor or a cancerated cell.

An operator inputs a boundary between the necessary area 41a and the unnecessary area 41b of the sample 41 to be collected to the control device 5 by the operation unit 18 while watching this image in the monitor 17, and specifies an area in which the DNA is destroyed by applying the laser light. The operation unit 18 can specify a laser irradiation range by operating the cursor in the monitor 17 by using, e.g., a mouse or a joy stick.

The control device 5 outputs a control signal to the micro mirror array 25 to reflect only an area that is to be irradiated with the laser light based on operation information 20 inputted from the operation unit 18. Therefore, a pattern reflecting the necessary area 41a and the unnecessary area 41b of the sample 41 is formed on the micro mirror array 25.

In place of specifying an area in which the DNA is destroyed by manipulating the operation unit 18 by an operator, a judgment condition of the necessary area 41a and the unnecessary area 41b of the sample 41 may be formulated in advance, and the control device 5 may automatically generate a pattern reflecting the necessary area 41a and the unnecessary area 41b of the sample 41 from an observation image of the sample 41.

Figure 9B:
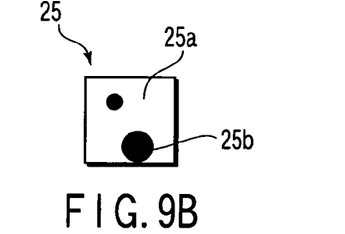
FIG. 9B shows a pattern formed on a micro mirror array.

FIG. 9B shows a pattern formed on the micro mirror array 25. Here, reference numeral 25a denotes an area in which the laser light is reflected along the optical path of the laser light irradiation optical system, and reference numeral 25b designates an area in which the laser light is not reflected along the optical path of the laser light irradiation optical system.

Figure 9C:
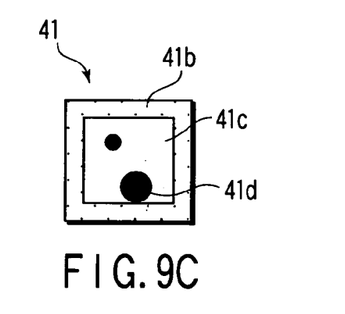
FIG. 9C shows a pattern image of the micro mirror array.

Here, when the pattern image projection light source 10 is turned on and the brightness of the sample observation light source 1 is reduced, an image of the pattern of the micro mirror array 25 projected onto the sample 41 by the pattern image projection light source 10 can be observed in the monitor 17. FIG. 9C shows an image of the pattern of the micro mirror array 25. Here, reference numeral 41c denotes an area that is irradiated with the laser light, and reference numeral 41d designates an area that is not irradiated with the laser light.

On this stage, a shape of the pattern may be corrected by the operation unit 18, if necessary.

When the shape of the pattern is determined, the unnecessary area is irradiated with the laser light to destroy the DNA.

Figure 9D:
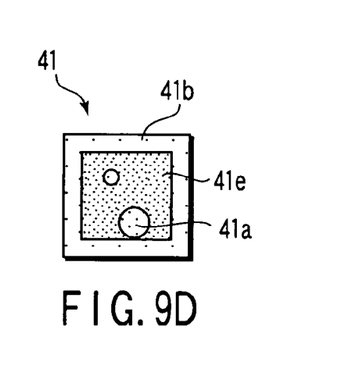
FIG. 9D shows an observation image of the sample after applying the laser light.

FIG. 9D denotes an observation image of the sample after irradiating the laser light. Here, reference numeral 41e denotes an area in which the DNA is destroyed by irradiation of the laser light.

Then, the sample 41 is moved by the XY stage 61, and any other part of the sample 41 is also irradiated with the laser light according to the pattern of the micro mirror array 25. Movement of the sample 41 and irradiation of the laser light according to the pattern of the micro mirror array 25 are repeatedly carried out for a necessary number of times in such a manner that the DNA in the unnecessary area 41b in a desired range is destroyed. Here, the desired range means a range containing an area to be collected including the necessary area 41a.

Figure 9E:
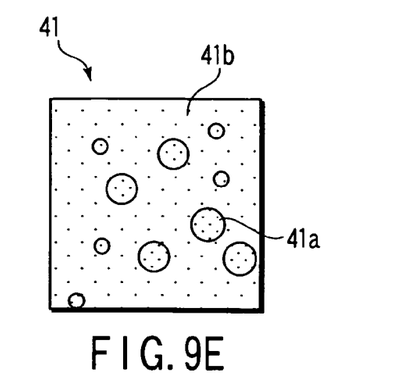
FIG. 9E shows an area of the sample that is wider than a range irradiated with the laser light in accordance with a pattern of the micro mirror array.
Figure 9F:
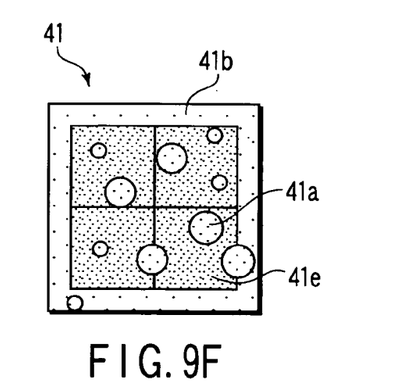
FIG. 9F shows a sample after performing irradiation of the laser light for the area depicted in FIG. 9E for four times while changing positions.

FIG. 9E shows a wider area of the sample 41 than the range that is irradiated with the laser light in accordance with the pattern of the micro mirror array 25. Further, FIG. 9F shows the sample 41 after irradiating the area depicted in FIG. 9E with the laser light according to the pattern of the micro mirror array 25 for four times while changing positions.

Subsequently, the relay lens 131 is removed from the optical path by the relay lens attachment/detachment mechanism 132. In this state, as shown in FIG. 8B, the laser light is converged by the objective lens 6, and the sample 41 is irradiated with this beam. A beam of laser light applied to the sample 41 has an energy that is sufficient for evaporating the sample 41.

The sample 41 is moved by the XY stage 61 while irradiating the sample 41 with the laser light, and a beam spot of the laser light is moved in, e.g., a circular form to surround an area to be collected including the necessary area 41a in the area 41e in which the DNA is destroyed. Therefore, the part of the sample irradiated with the laser light is evaporated, and the area to be collected including the necessary area 41a is cut from the sample 41.

Figure 9G:
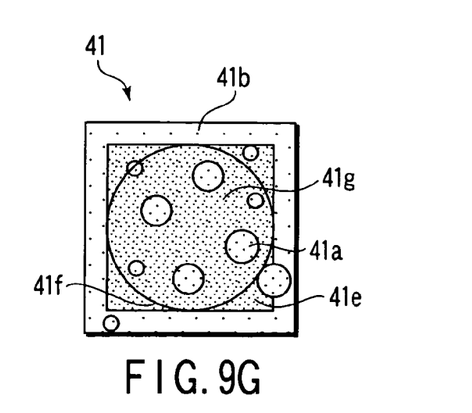
FIG. 9G shows a sample from which an area to be collected including a necessary area is cut.

FIG. 9G shows the sample 41 from which the area to be collected including the necessary area 41a is cut. Here, reference numeral 41f denotes a part that the sample 41 is evaporated by irradiation of the laser light, and reference numeral 41g designates an area to be collected including the necessary area 41a. In this embodiment, the area 41a required for analysis does not match with the area 41g to be collected, and the area 41g to be collected including the area 41a required for analysis.

Figure 10A:
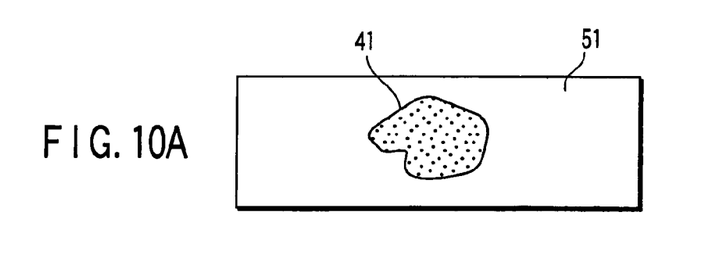
FIG. 10A shows a sample before performing microdissection according to a third embodiment.
Figure 10B:
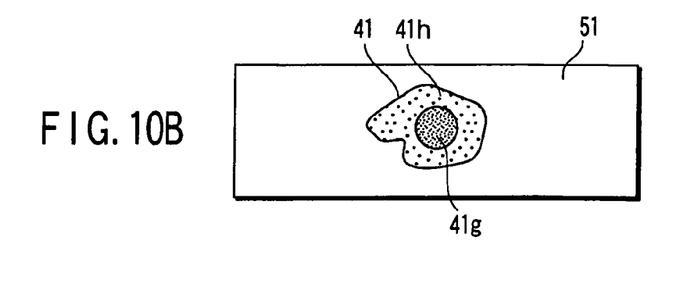
FIG. 10B shows a sample after performing microdissection according to the third embodiment.

FIG. 10A shows the sample 41 before performing microdissection according to the third embodiment of the present invention. FIG. 10B shows the sample 41 after conducting microdissection according to the third embodiment of the present invention.

By carrying out microdissection according to this embodiment to the sample 41 depicted in FIG. 10A by the above-described operation procedure, the area 41g to be collected including the necessary area 41a is cut from the remaining area 41h of the sample 41.

According to this embodiment, extensive irradiation of the laser light according to the pattern of the active optical element and convergent irradiation of the laser light can be easily switched. Therefore, destruction of the DNA in the unnecessary area of the sample and cutting of the area of the sample 41 to be collected can be readily carried out by one apparatus.

When using an objective lens with a low magnification, there is the possibility that the light intensity deficiency may occur by entire irradiation on a visual field surface because the visual field is wide. In such a case, the light intensity deficiency can be avoided by removing the relay lens and switching to point irradiation. For example, if a magnification of the objective lens to be used is decuple, an area of the visual field becomes 16-fold of that when using the objective lens whose magnification is 40-fold.

When destroying the DNA in the unnecessary area of the sample, it is good enough to arrange the relay lens in the optical path and irradiating a wide range of the sample 41 with the laser light with the energy density sufficient for destroying the DNA. Furthermore, when cutting the area of the sample to be collected, it is good enough to remove the relay lens from the optical path and move a beam spot of the laser light on the sample 41 along the area to be collected while irradiating a narrow range of the sample 41 with the laser light with the energy density sufficiently high to evaporate the sample.

Modification

In the third embodiment, the erecting microscope type microdissection apparatus using the reflection type active optical element has an apparatus structure in which the relay lens can be attached/detached to/from the optical path of the laser light. However, the inverted microscope type microdissection apparatus using the transmission type active optical element may have an apparatus structure that the relay lens has appropriate optical characteristics according to needs and can be attached/detached to/from the optical path of the laser light.

That is, the inverted microscope type microdissection apparatus using the transmission type active optical element depicted in FIG. 1 or 3 may have an apparatus structure that the relay lens can be attached/detached to/from the optical path of the laser light. Moreover, the erecting microscope type microdissection apparatus using the transmission type active optical element depicted in FIG. 4 may have an apparatus structure that the relay lens can be attached/detached to/from the optical path of the laser light. The inverted microscope type microdissection apparatus using the reflection type active optical element depicted in FIG. 5 may have an apparatus structure that the relay lens can be attached/detached to/from the optical path of the laser light.

By doing so, the same advantages as those in the third embodiment can be expected.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:
1. A microdissection apparatus comprising:
a laser light source to emit laser light; and a laser light irradiation optical system to irradiate a sample with the laser light from the laser light source;

wherein the laser light irradiation optical system comprises: (i) an active optical element on which a variable pattern set to correspond to a necessary area is formed, and (ii) an objective lens which is positioned between the active optical element and the sample; and wherein the laser light is irradiated through the active optical element on which the variable pattern is formed, and guided to the sample by the objective lens so that a part of the sample excluding the necessary area is irradiated with the laser light.

2. The microdissection apparatus according to claim 1, further comprising a pattern image projection optical system, which projects an image of the pattern formed on the active optical element onto the sample.

3. The microdissection apparatus according to claim 2, further comprising an observation optical system, which acquires an observation image of the sample.

4. The microdissection apparatus according to claim 3, further comprising a display unit to display the observation image acquired by the observation optical system, and an input unit to input information for setting the pattern formed on the active optical element.

5. The microdissection apparatus according to claim 3, further comprising a control unit to set the pattern formed on the active optical element based on the observation image acquired by the observation optical system.

6. The microdissection apparatus according to claim 1, wherein the laser light irradiation optical system selectively irradiates a part of the sample that surrounds the necessary area with the laser light in accordance with the pattern formed on the active optical element, and the laser light applied to the sample has an energy density sufficient for evaporating the sample, such that the part of the sample irradiated with the laser light is evaporated so as to cut the necessary area from the sample.

7. The microdissection apparatus according to claim 1, wherein the laser light irradiation optical system further comprises a relay lens which is removably inserted into an optical path between the active optical element and the objective lens, and a relay lens insertion/removal mechanism to insert and remove the relay lens into and from the optical path;

wherein when the relay lens is inserted in the optical path, the active optical element forms the pattern corresponding to the necessary area, and the laser light irradiation optical system selectively irradiates the part of the sample excluding the necessary area with the laser light in accordance with the pattern formed on the active optical element; and wherein when the relay lens is removed from the optical path, the laser light irradiation optical system converges a beam of laser light by the objective lens to irradiate the sample with the converged beam.

8. The microdissection apparatus according to claim 7, wherein, when the relay lens is removed from the optical path, the converged beam of laser light has an energy density sufficient for evaporating the sample.

9. The microdissection apparatus according to claim 8, further comprising a movement mechanism, which relatively moves the sample and a beam spot of the converged beam of laser light formed on the sample;

wherein the beam spot of the laser light is relatively moved on the sample by the movement mechanism completely around an area to be collected including the necessary area, and a part of the sample irradiated with the converged beam of laser light is evaporated to be cut, such that the area to be collected including the necessary area is cut from the sample.

10. The microdissection apparatus according to claim 1, wherein the active optical element comprises a transmission type active optical element.

11. The microdissection apparatus according to claim 1, wherein the active optical element comprises a reflection type active optical element.

12. A microdissection apparatus comprising:
a light source means for emitting laser light; and
a laser light irradiation optical system to irradiate a sample with the laser light from the light source means;

wherein the laser light irradiation optical system comprises: (i) pattern forming means for transmitting or reflecting the laser light selectively in accordance with a variable pattern which is set to correspond to a necessary area, and (ii) an objective lens which is positioned between the pattern forming means and the sample; and wherein the laser light is irradiated to the sample through the variable pattern formed by the pattern forming means, and guided to the sample by the objective lens so that a part of the sample excluding the necessary area is irradiated with the laser light.

13. The microdissection apparatus according to claim 12, further comprising a pattern image projection optical system for projecting an image of the pattern formed by the pattern forming means onto the sample.

14. The microdissection apparatus according to claim 13, further comprising an observation optical system for acquiring an observation image of the sample.

15. The microdissection apparatus according to claim 14, further comprising displaying means for displaying the observation image acquired by the observation optical system, and inputting means for inputting information for setting the pattern formed by the pattern forming means.

16. The microdissection apparatus according to claim 14, further comprising a controller for setting the pattern formed by the pattern forming means based on the observation image acquired by the observation optical system.

17. The microdissection apparatus according to claim 12, wherein the laser light irradiation optical system selectively irradiates a part of the sample that surrounds the necessary area with the laser light in accordance with the pattern formed by the pattern forming means, and the laser light applied to the sample has an energy density sufficient for evaporating the sample, such that the part of the sample irradiated with the laser light is evaporated so as to cut the necessary area from the sample.

18. The microdissection apparatus according to claim 12, wherein the laser light irradiation optical system further comprises a relay lens, which is removably inserted into an optical path between the pattern forming means and the objective lens, and a relay lens insertion/removal mechanism, which inserts and removes the relay lens into and from the optical path;

wherein when the relay lens is inserted in the optical path, the pattern forming means forms the pattern corresponding to the necessary area, and the laser light irradiation optical system selectively irradiates the part of the sample excluding the necessary area with the laser light in accordance with the pattern formed on the pattern forming means; and wherein when the relay lens is removed from the optical path, the laser light irradiation optical system converges a beam of laser light by the objective lens to irradiate the sample with the converged beam.

19. The microdissection apparatus according to claim 18, wherein, when the relay lens is removed from the optical path, the converged beam of laser light has an energy density sufficient for evaporating the sample.

20. The microdissection apparatus according to claim 19, further comprising moving means for relatively moving the sample and a beam spot of the converged beam of laser light formed on the sample;
wherein the beam spot of the laser light is relatively moved on the sample by the moving means completely around an area to be collected including the necessary area, and a part of the sample irradiated with the converged beam of laser light is evaporated to be cut, such that the area to be collected including the necessary area is cut from the sample.

21. The microdissection apparatus according to claim 12, wherein the pattern forming means comprises a transmission type active optical element.

22. The microdissection apparatus according to claim 12, wherein the pattern forming means comprises a reflection type active optical element.

23. A microdissection method comprising:
forming a variable pattern on an active optical element such that the pattern is set to correspond to a necessary area of a sample; and
irradiating the active optical element with laser light; and
guiding the laser light from the active optical element to the sample, via an objective lens positioned between the active optical element and the sample, so as to irradiate a part of the sample excluding the necessary area with the laser light.

24. The microdissection method according to claim 23, wherein a part of the sample which surrounds the necessary area is selectively irradiated with the laser light in accordance with the pattern formed on the active optical element and is evaporated, thereby cutting the necessary area from the sample.

25. The microdissection method according to claim 24, further comprising:
projecting an image of the pattern formed on the active optical element onto the sample;
obtaining an observation image of the sample; and
setting the pattern formed on the active optical element based on the obtained observation image.

26. The microdissection apparatus according to claim 23, wherein the part of the sample excluding the necessary area is selectively irradiated with the laser light in accordance with the pattern formed on the active optical element, and the selective irradiation of the laser light is repeatedly performed while changing positions on the sample that are irradiated to irradiate all desired positions on the sample; and
wherein the method further comprises converging a beam of the irradiated laser light onto a beam spot on the sample; and
relatively moving the beam spot of the converged beam of laser light with respect to the sample completely around an area to be collected including the necessary area;
wherein a part of the sample irradiated with the converged beam of laser light is evaporated, such that the area to be collected including the necessary area is cut from the sample.

27. The microdissection apparatus according to claim 1, further comprising an observation optical system, which acquires an observation image of the sample.

28. The microdissection apparatus according to claim 27, wherein the observation optical system comprises an erecting microscope.

29. The microdissection apparatus according to claim 27, wherein the observation optical system comprises an inverted microscope.

30. The microdissection apparatus according to claim 3, wherein the objective lens of the laser light irradiation optical system is also part of the observation optical system.

31. The microdissection apparatus according to claim 27, wherein the objective lens of the laser light irradiation optical system is also part of the observation optical system.

32. The microdissection apparatus according to claim 3, wherein the observation optical system comprises an erecting microscope.

33. The microdissection apparatus according to claim 3, wherein the observation optical system comprises an inverted microscope.

34. The microdissection apparatus according to claim 10, wherein the transmission type active optical element comprises a liquid crystal substrate.

35. The microdissection apparatus according to claim 11, wherein the reflection type active optical element comprises a micro mirror array.

36. The microdissection apparatus according to claim 1, wherein the laser light irradiation optical system selectively irradiates a part of the sample that surrounds the necessary area with the laser light in accordance with the pattern formed on the active optical element, the laser light applied to the sample is relatively moved on the sample by a movement mechanism completely around an area to be collected including the necessary area, and a part of the sample irradiated with the converged beam of laser light is evaporated to be cut, such that the area to be collected including the necessary area is cut from the sample.

* * * * *